United States Patent [19]

Vértesy et al.

[11] Patent Number: 5,302,582
[45] Date of Patent: Apr. 12, 1994

[54] ENKASTINS: NEW GLYCOPEPTIDES WHICH ACT TO INHIBIT ENKEPHLINASE, PROCESSES FOR THEIR PREPARATION, AND THEIR USE AS PHARMACEUTICAL PRODUCTS

[75] Inventors: László Vértesy, Eppstein/Taunus; Peter Schindler, Mörfelden-Walldorf; Herbert Kogler, Kelkheim; Hans-Wolfram Fehlhaber, Idstein/Taunus, all of Fed. Rep. of Germany; Francoise Delevallée, Fontenay-sous-bois, France

[73] Assignee: Hoechst Aktiengesellschaft, Frankfurt am Main, Fed. Rep. of Germany

[21] Appl. No.: 727,388

[22] Filed: Jul. 5, 1991

Related U.S. Application Data

[63] Continuation of Ser. No. 185,028, Apr. 22, 1988, abandoned.

[30] Foreign Application Priority Data

Apr. 25, 1987 [DE] Fed. Rep. of Germany ....... 3713873
Nov. 20, 1987 [DE] Fed. Rep. of Germany ....... 3739376

[51] Int. Cl.$^5$ .................. C07H 7/02; A61K 31/70
[52] U.S. Cl. ........................................ 514/23; 514/8; 536/29.2; 530/322
[58] Field of Search .............. 530/322; 514/18, 23; 536/29.2

[56] References Cited

PUBLICATIONS

Heyns et al., Chemische Brichte Jahrg, vol. 90, pp. 1374–1387 (1957).
Chemical Abstracts, vol. 54, No. 3239e (1959).
P. Finot, Diabetes, vol. 31, Supp. 3, pp. 22–28 (1982).
K. Heyns and H. Paulsen, Liebigs Ann. Chem. 622, (1959) pp. 160–174.
H. Roper et al., Carbohydrate Res. 116, (1983) pp. 183–195.
B. N. Stepaneko and N. N. Borodina, Prikl. Biokhim. Mikrobiol. 12(1), (1976), pp. 5–13.
C. A. 85: 143425h.
R. E. Chipkin, Drugs of the Future, vol. 11, (1986), pp. 593–606.
M. Pozsgay et al., Biochemistry, vol. 25, (1986), pp. 1292–1299.

*Primary Examiner*—David B. Springer
*Attorney, Agent, or Firm*—Finnegan, Henderson, Farabow, Garrett & Dunner

[57] ABSTRACT

The invention relates to new biologically active glycopeptides of the general formula $$\text{Sacch}-\text{A}-\text{B}-\text{R}$$

in which Sacch represents a monosaccharide residue with, where appropriate, the OH groups being partially or completely substituted,
A represents the residue of a neutral L- or D-amino acid or —if B is absent—represents the residue of a neutral D-amino acid,
B is absent or represents the residue of a neutral L- or D-amino acid or of an optionally ω-substituted bifunctional acidic or basic L- or D-amino acid, and R represents hydroxyl, ($C_1$–$C_8$)-alkoxy, an amino radical which is optionally substituted by one or two identical or different radicals from the series comprising ($C_1$–$C_8$)-alkyl, ($C_5$–$C_8$)-cycloalkyl, ($C_5$–$C_8$)-heteroalkyl or ($C_5$–$C_8$)-heteroaryl, or another acid derivative. These compounds have enkephalinase-inhibiting properties and can thus be used, for example, as analgesics in human and veterinary medicine. The isolation of these compounds from Streptomyces albus ATCC 21838, and further processes for their preparation, are also described.

5 Claims, 5 Drawing Sheets

ENKASTINS: NEW GLYCOPEPTIDES WHICH ACT TO INHIBIT ENKEPHLINASE, PROCESSES FOR THEIR PREPARATION, AND THEIR USE AS PHARMACEUTICAL PRODUCTS

This application is a continuation, of application Ser. No. 07/185,028, filed Apr. 22, 1988.

The invention relates to new, biologically active glycopeptides. They have enkephalinase-inhibiting properties and thus can be used, for example, as analgesics in human and veterinary medicine. Processes for their preparation are described.

Enkastins are compounds in which a monosaacharide is linked via an amine nitrogen to an amino acid or a dipeptide. Compounds of this type with an L-amino acid have been described by K. Heyns and H. Paulsen (Liebigs Ann. Chem. 622 (1959) 160-174) and H. Röper, S. Röper and K. Heyns (Carbohydrate Research 116 (1983) 183-195). Compounds such as N-(1-deoxy-β-D-fructopyranos-1-yl)-Gly-Gly-OH and N-(1-deoxy-β-D-fructopyranos-1-yl)-Gly-Ser-OH have already been disclosed by B. N. Stepanenko and N. N. Borodina, Prikl. Biokhim. Mikrobio. 12 (1) (1976) 5-13 [C.A. 85: 143425 h].

Various classes of compounds have been described as enkephalinase-inhibitors having analgesic activity. They have in common a functional group adjacent to a lipophilic amino acid, which can enter into a coordination compound with the $Zn^{2+}$, which is essentially involved in the catalysis, of this metalloenzyme. Examples of these functional groups include —SH, HO—N-H—CO—, —P(=O)OH—R and —COOH (R. E. Chipkin, Drugs of the Future 11 (7) (1986), 593-606). It is also known that such compounds inhibit not only enkephalinase but also the enzyme thermolysin which can be isolated from bacteria (M. Pozsgay, C. Michaud, M. Liebmann and M. Orlowski, Biochemistry 25 (1986) 1292-1299).

Hence the object of the invention is to find compounds which specifically inhibit enkephalinase.

This object is achieved according to the invention by the compounds of the general formula I Sacch—A—B—R    (I)

in which Sacch represents a monosaccharide residue with, where appropriate, the OH groups being partially or completely substituted, A represents the residue of a neutral L- or D-amino acid or —if B is absent—represents the residue of a neutral D-amino acid, B is absent or represents the residue of a neutral L- or D-amino acid or of an optionally ω-substituted bifunctional acidic or basic L- or D-amino acid, and R represents hydroxyl, $(C_1-C_8)$-alkoxy, an amino radical which is optionally substituted by one or two identical or different radicals from the series comprising $(C_1-C_8)$-alkyl, $(C_5-C_8)$-cycloalkyl, $(C_5-C_8)$-heteroalkyl or $(C_5-C_8)$-heteroaryl, or another acid derivative, or their physiologically tolerated salts, with the proviso that the compounds N-(1-deoxy-β-D-fructopyranos-1-yl)-Gly-Gly-OH and N-(1-deoxy-β-D-fructopyranos-1-yl)-Gly-Ser-OH are excepted.

Particularly suitable salts are alkali metal and alkaline earth metal salts, salts with physiologically tolerated amines, and salts with inorganic and organic acids such as, for example, HCl, HBr, $H_2SO_4$, $H_3PO_4$, maleic acid, fumaric acid, citric acid, tartaric acid and acetic acid.

Where the OH groups of the monosaccharide residue are substituted they are preferably etherified or esterified, in particular by $(C_1-C_4)$-alkoxy or $(C_1-C_4)$-alkylcarbonyl. In addition, the OH groups can also be replaced by hydrogen (deoxy sugars), $(C_1-C_4)$-alkyl, and heteroatoms such as O, N, S and their derivatives.

Unless otherwise indicated in the specific case, alkyl and alkoxy can be straight-chain or branched.

Particularly suitable as heteroalkyl are cyclic compounds. In the same was as with heteroaryl, these are particularly to be understood to be nitrogen-containing compounds such as, for example, pyrrolidine, piperidine and pyridine.

The preferred residues A and B are those derived from naturally occurring α-amino acids (see, for example, Schröder, Lübke, "The Peptides", Volume I, New York 1965, pages 137-270 or Houben-Weyl, "Methoden der organischen Chemie" (Methods of organic chemistry) volume 15/1 and 2, supplement), their antipodes or their simple metabolites. The chirality centers in the peptides can each have the R or S or R,S configuration.

The amino acids are described hereinafter by the symbols used in L. Styrer, "Biochemistry" (W. H. Freeman & Company, San Francisco, 1972, pages 14 et seq.). The symbol "D" is prefixed to these symbols in the case of the residue of a D-amino acid; residues without a configuration symbol have the L configuration.

Sacch can be, for example, a triose, tetrose or a furanosyl or pyranosyl radical derived from aldopentoses, aldohexoses, ketopentoses, ketohexoses, Deoxyaldoses and aminoaldoses, as well as the stereoisomers, in particular from D- or L-monosaccharides such as ribose (Rib), arabinose (Ara), xylose (Xyl), Lyxose (Lyx), allose (All), altrose (Alt), glucose (Glc), mannose (Man), gulose (Gul), idose (Ido), galactose (Gal), talose (Tal), erythrose (Ery), threose (Thr), psicose (Psi), fructose (Fru), sorbose (Sor), tagatose (Tag), xylulose (Xyu), fucose (Fuc), rhamnose (Rha), olivose (Oli), oliose (Olo), mycarose (Myc), rhodosamine (RN), N-acetylglucosamine (GlcNAc), N-acetylgalactosamine (GalNAc), N-acetylmannosamine (ManNAc) and their synthetic derivatives such as deoxy-, amino-, acetamido-, halogeno-, preferably bromo- or iodo-, sugars or inositol. Sacch can be in the α or β form, but is preferably in the β form, and can also be in the form of a monosaccharide derivative.

Preferred glycopeptides of the formula I are those in which

Sacch denotes the residue of an aldohexose or ketohexose or their derivatives,

A denotes Ile, Phe, Leu, Val, Thr, Ser, Gly, Cys, Ala or hexahydrophenylglycine (Hhp), in each case in the L or D form, or —where B is absent—each of the preceding residues in the D form, B is absent or denotes Asp, Asx, Glu, Glx, Ser, Thr or Gly, in each case in the L or D form, and R denotes hydroxyl or as well as their physiologically tolerated salts, exceptions being made of the compounds N-(1-deoxy-β-D-fructopyranos-1-yl)-Gly-Gly-OH and N-(1-deoxy-β-D-fructopyranos-1-yl)-Gly-Ser.

Glycopeptides of the formula I in which
Sacch denotes fructosyl or its derivatives,
A denotes Ile, Phe, Leu, Val, Cys, Ala or Hhp, in each case in the L or D form, or—where B is absent—each of the preceding residues in the D form,
B is absent or denotes Asp, Asx, Glu or Ser, in each case in the L or D form, and
R denotes hydroxyl,
and their physiologically tolerated salts, are particularly preferred.

Also especially preferred are those glycopeptides of the formula I in which
Sacch denotes fructosyl or its derivatives,
A denotes Ile, Leu, Val, Cys or Hhp, in each case in the D form,
B denotes Asp, Asx, Glu or Ser, in each case in the L or D form, and
R denotes hydroxyl,
and their physiologically tolerated salts.

Special mention may be made of the following glycopeptides:

Enkastin ID, Enkastin (D)ID

N-(1-deoxyfructopyranos-1-yl)-Ile-Asp-OH
N-(1-deoxyfructopyranos-1-yl)-D-Ile-Asp-OH Enkastin VD, Enkastin (D)VD

N-(1-deoxyfructopyranos-1-yl)-Val-Asp-OH
N-(1-deoxyfructopyranos-1-yl)-D-Val-Asp-OH Enkastin AD

N-(1-deoxyfructopyranos-1-yl)-Ala-Asp-OH

Enkastin IE

N-(1-deoxyfructopyranos-1-yl)-Ile-Glu-OH

Enkastin VE

N-(1-deoxyfructopyranos-1-yl)-Val-Glu-OH

Enkastin AE

N-(1-deoxyfructopyranos-1-yl)-Ala-Glu-OH

Enkastin (D)V

N-(1-deoxyfructopyranos-1-yl)-D-Val-OH

The invention also relates to a process for the preparation of the compounds of the formula I, which comprises
a) cultivation of Streptomyces albus (ATCC 21838), as well as its variants and mutants, in a nutrient medium until compounds of the formula I in which Sacch represents an N-(1-deoxyfructopyranos-1-yl) residue, A represents Ala, Leu, Val or Ile, B represents Asp or Glu, and R represents hydroxyl, accumulate in the culture and, where appropriate,
b) isolation, purification and derivatisation thereof.

In a nutrient solution which contains a source of carbon and a source of nitrogen as well as the customary inorganic salts, Streptomyces albus ATCC 21838 produces, inter alia, enkastin ID, enkastin VD, enkastin AD, enkastin IE, enkastine VE and enkastin AE.

Of course, it is also possible to use in place of the strain ATCC 21838 its variants and mutants as long as they synthesize at least one of these compounds. Mutants of this type can be generated in a manner known per se, by physical agents, for example irradiation, such as with ultraviolet or X-rays, or chemical mutagens such as, for example, ethyl methanesulfonate (EMS) or 2-hydroxy-4-methoxybenzophenone (MOB).

Sources of carbon which are suitable and preferred for the aerobic fermentation are assimilable carbohydrates and sugar alcohols such as glucose, lactose or D-mannitol, as well as carbohydrate-containing natural products such as malt extract, as well as oils and fats. Suitable nitrogen-containing nutrients are: amino acids, peptides and proteins, as well as their degradation products, such as peptones or tryptones, further meat extracts, ground seeds, for example of corn, wheat, beans, soybeans or the cotton plant, distillation residues from the production of alcohol, meat meals or yeast extracts, as well as ammonium salts and nitrates. Examples of other inorganic salts which the nutrient solution can contain are chlorides, carbonates, sulfates or phosphates of the alkali metal or alkaline earth metals, or trace elements such as, for example, iron, zinc, cobalt and manganese.

The production of the enkastins takes place especially satisfactorily in a nutrient solution which contains 0.1 to 15% of nutrient constituents such as soybean flour, soybean oil and mannitol, in particular 0.1 to 3% of each, based on the total weight of the nutrient solution. The fermentation is carried out aerobically, that is to say, for example, submerged with shaking or stirring in shaken flasks or fermenters, where appropriate with the introduction of air or oxygen. The fermentation can be carried out in a temperature range from about 18° to 35° C., preferably at about 25° to 30° C., in particular at 28° to 30° C. The pH range should be between 6 and 8, advantageously between 6.5 and 7.5. Under these conditions, the enkephalinase-inhibiting action of the culture broth is considerable after 6 to 15 days, in general.

The cultivation is advantageously carried out in several stages, i.e. initially one or more precultures are prepared in a liquid nutrient medium and are then transferred into the actual production medium, the main culture, for example in the ratio by volume 1:10. The preculture is obtained by, for example, transferring a sporulated mycelium into a nutrient solution and allowing it to grow for about 80 to 400 hours. The sporulated mycelium can be obtained by allowing the strain to grow for about 12 days on a solid or liquid nutrient medium, for example yeast/malt agar.

The progress of the fermentation can be monitored by means of the pH of the culture or the volume of the mycelia or by testing the biological activity. The enkastins are present both in the mycelium and in the culture filtrate. However, the principal amount of the enkastins is generally to be found in the culture filtrate.

The said compounds are isolated from the culture medium by known methods, taking into account the chemical, physical and biological properties of the products, such as, for example, chromatography on ion exchangers, molecular sieves, adsorption resins and reversed phase supports, by solvent precipitations, reverse osmosis and others.

It is also advantageous to separate the aqueous phase from the mycelium, for example by filtration or centrifugation, and to isolate and purify the enkastins from the relevant phases.

A preferred process comprises removing fats from the culture filtrate by extraction with butanol, and concentrating the aqueous phase in vacuo. The aqueous concentrate is diluted with 2 to 5 times the amount of methanol and is centrifuged to remove the precipitated high molecular weight substances. The aqueous methanolic supernatant is then treated with strongly acid ion exchangers, such as, for example ®Dowex 50 WX 2, to isolate the basic substances first, and then with an anion exchanger, such as, for example ®Amberlite IRA-68, to isolate the amphoteric substances therefrom. The latter fraction contains the enkastins. After removal of salts using a molecular sieve such as, for example, ®Sephadex G-15, the individual enkastin components are obtained by preparative HPLC, for example on reversed phase RP-18.

However, it is also possible to prepare the enkastins in other ways (synthetically). Hence the invention relates to a further process for the preparation of the compounds of the formula I, which comprises a) condensation of an amino acid having a free N-terminal amino group with an amino acid having a free C-terminal carboxyl group, where appropriate elimination of one or more protective groups which have been temporarily introduced to protect functional groups where appropriate, b) condensation of the dipeptide or of an amino acid having a free N-terminal amino group with a monosaccharide having a free hydroxyl group at the anomeric center, where appropriate elimination of one or more protective groups temporarily introduced to protect functional groups where appropriate, c) conversion of the resulting N-glycoside, where appropriate by Amadori rearrangement, into the N-substituted iso-sugar amines, and conversion of the resulting enkastin into, where appropriate, its physiologically tolerated salt or its derivative, it also being possible to interchange the sequence of these reactions and-where an amino acid is used in b)-to omit a).

However, other reactions which are known per se are also suitable for forming the sugar-NH-peptide bond.

The selection of the protective groups and the synthetic strategy is determined by the nature and configuration of the amino acids and the nature of the coupling conditions.

The condensation of the amino acids to give the dipeptides by the process according to the invention is carried out by the customary methods of peptide chemistry, preferably by the mixed anhydride method, via active esters, azides or by the carbodiimide method, in particular with the addition of substances which increase the reaction rate and prevent racemisation, such as, for example, 1-hydroxybenzotriazole, N-hydroxysuccinimide, 3-hydroxy-4-oxo-3,4-dihydro-1,2,3-benzotriazine or N-hydroxy-5-norbornene-2,3-dicarboximide, as well as by using activated derivatives of 1-hydroxybenzotriazole or anhydrides of phosphoric, phosphonic and phosphinic acids, at a reaction temperature between $-10°$ C. and the boiling point of the reaction mixture, preferably between $-5°$ C. and 40° C.

Solvents suitable for this are dimethylformamide, dimethylacetamide, hexamethylphosphoric triamide, N-methylpyrrolidone or dimethyl sulfoxide. Where the solubility of the components permits it, it is also possible to use solvents such as methylene chloride or chloroform. The methods mentioned are described in, for example, Meienhofer-Gross: "The Peptides", Academic Press, Vol. I, (1979).

In order to condense the glycosyl radical onto the amino acid or the dipeptide, it is possible for the carboxyl group, and other functional groups not involved in the reaction, to be suitably protected beforehand. The protective groups which have proved particularly suitable for this are those which can be eliminated by catalytic hydrogenation, such as, for example, the benzyl (OBzl) or p-nitrobenzyl (ONbzl) esters. Other suitable protective groups are described by, for example, Hubbuch, Kontakte Merck 3 (1979) pages 14 to 23 and Büllesbach, Kontakte Merck 1 (1980) pages 23 to 35.

Protective groups customary in carbohydrate chemistry are to be understood to be, for example, the $(C_1-C_{10})$-acyl protective groups such as $(C_1-C_6)$-alkanoyl (for example acetyl, trichloroacetyl and trifluoroacetyl), benzoyl or p-nitrobenzoyl, as well as optionally modified methyl, methyloxymethyl, benzyl, tetrahydropyranyl, benzylidene, isopropylidene or trityl groups, preference being given in this case to the acyl protective groups, in particular the acetyl (Ac) group.

The synthesis of the enkastins entails the linkage of two polyfunctional reactants (carbohydrate and amino acid or dipeptide). It must be possible for both to be selectively blocked and unblocked. It must be possible to liberate and functionalize the anomeric center in the glycosyl component, and it is permissible in the amino acid component for only the amino group which is necessary for the linkage to be unblocked. It is necessary, depending on the type of glycosidic bond intended (1,2-cis- or 1,2-trans-glycosides), to introduce suitable protective groups to block the hydroxyl or amino groups in the glycosyl component and, where appropriate, to work out reaction conditions for the linkage step which leads stereoselectively to only one of the two possible anomers.

The synthesis of N-(1-deoxyfructos-1-yl)-L-amino acids has already been described several times (see, for example, H. Röper et al. Carbohydrate Research, 116 (1983) 183-195). This entails the unsubstituted reactants being dissolved in water or water/methanol and heated with various buffers or additives such as, for example, sodium pyrosulfite. The yields vary with the nature of the starting material and average 20%.

It has now been found, surprisingly, that the reaction of sugars with amino acids or peptides having free amino groups can be carried out to give the desired Amadori products in very good yields, i.e. above 90% in some cases, in the presence of, i.e. with catalysis by, secondary or tertiary, aliphatic or aromatic, nitrogen-containing compounds such as, for example, pyridine, dimethylaminopyridine, di-($C_1$-$C_8$)-alkyl- and tri-($C_1$-$C_8$)-alkylamines, ($C_6$-$C_{12}$)-aryl-($C_1$-$C_8$)-alkylamines, tris buffer, dimethylformamide or imidazole. The solvents used are pyridine, water, aqueous methanol, methanol, ethanol, dimethyl sulfoxide (DMSO) or others, as well as mixtures thereof, but preferably anhydrous pyridine or the latter mixed with anhydrous methanol, DMSO and other solvents. The reaction temperature can be varied within a wide range. Possible temperatures are between 0° C. and 250° C. However, one between room temperature and 120° C. is preferably employed. The reaction time depends on the temperature and ranges from a few seconds to some days. A typical reaction takes 2 hours at 65° C. Substantial reaction is indicated by the yellow-gold coloration of the originally colorless reactants. On continuation of the reaction the reaction mixture assumes an increasingly deeper brown color, with diminution in yield (Mailland reaction).

It is possible to use as reactants unprotected or partially derivatized sugars having unsubstituted aldehyde or keto groups, as well as unprotected or derivatized amino acids and peptides having free amino groups. Suitable sugars are all known trioses, tetroses, pentoses, hexoses, heptoses, deoxy sugars etc.

The Amadori rearrangement (cf. Weygand/Hilgetag, "Organischchemische Experimentierkunst" (The art of organic chemical experimentation) J. A. Barth-Verlag Leipzig (1964) 980) is effected by leaving the N-glycoside to stand for 10 minutes to 10 days—preferably 0.5 to 3 days—at a temperature of 0° to 200° C.—in particular at 40° to 70° C., then removing water—where appropriate by azeotropic distillation—leaving to stand again, and subsequently drying the N-substituted iso-sugar amine.

The enkephalinase inhibitors according to the invention are of great interest, particularly for the treatment of painful conditions such as, for example, toothache, pain associated with colic, pain caused by heat or acids, pain generated by stress, and pain in the terminal stage of cancer. Furthermore, enkephalinase inhibitors of the formula I are also suitable for treatment of states of mental stress.

It is known that, for example, sensations of pain and anxiety states result in rapid release of endogenous enkephalins which suppress, by interaction with so-called opiate receptors, the action of these stimuli. However, enkephalins are, as appropriate for their function as neurotransmitters, rapidly degraded to inactive peptides by enkephalin-specific peptidases, and especially by the enzyme enkephalinase [EC 3.4.24.11]. Thus the consequence of inhibition of this degradation by enkephalinase inhibitors of the formula I is that endogenously released enkephalins are able to display their action on opiate receptors, and thus their pain- and anxiety-suppressing action, over a longer period.

The specific properties of the compounds on which this invention is based can be further characterized by the fact that they not only inhibit the degradation of enkephalins by enkephalinase but also have an intrinsic analgesic action. Hence it appears possible that the enkephalinase inhibitors characterized by the formula I also exert a direct action on opiate receptors.

Enkephalinase assay

The enkephalinase-inhibiting properties of the enkastins have been measured by methods known from the literature, and have been described by, for example Roques, B. P. et al. [Life Sciences (1982), 1749-1752]. The enzyme used was an enkephalinase preparation solubilized from rat kidneys by methods known per se [Mumford, R. A. et al. 1982, Biochem. Biophys. Res. Comm. 109, 1303-1309]. The 50% inhibition of enkephalinase by the compounds according to the invention, i.e. the $IC_{50}$ value, was determined in a known manner using a concentration series, and the inhibitors, to which the invention relates, having been preincubated with the enzyme at room temperature for 60 minutes before the enzymatic reaction was started by addition of the substrate. Suitable checks for the non-inhibited reaction were carried out in the absence of an inhibitor.

Enkephalinase inhibition

| | $IC_{50}$[mol/l] |
| --- | --- |
| 1. N-(1-deoxyfructos-1-yl)-D-Val-Asp | $1.3 \times 10^{-9}$ |
| 2. N-(1-deoxyfructos-1-yl)-D-Ile-Asp | $1.8 \times 10^{-9}$ |
| 3. N-(1-deoxyfructos-1-yl)-Ile-Asp | $1.8 \times 10^{-9}$ |
| 4. N-(1-deoxyfructos-1-yl)-Val-Asp | $6.3 \times 10^{-9}$ |
| 5. N-(1-deoxyfructos-1-yl)-Phe-Glu | $5.6 \times 10^{-8}$ |
| 6. N-(1-deoxyfructos-1-yl)-Val-Glu | $3.4 \times 10^{-8}$ |
| 7. N-(1-deoxyfructos-1-yl)-Ile-Asp | $3.4 \times 10^{-8}$ |
| 8. N-(1-deoxyfructos-1-yl)-Ile-Glu | $5.6 \times 10^{-8}$ |
| 9. N-(1-deoxyfructos-1-yl)-Ile-Asp(OtBu) | $7.0 \times 10^{-8}$ |
| 10. N-(1-deoxyfructos-1-yl)-Hhp-Asp | $7.5 \times 10^{-8}$ |
| 11. N-(1-deoxyfructos-1-yl)-Ile-Ser | $2.1 \times 10^{-7}$ |
| 12. N-(1-deoxyfructos-1-yl)-D-Val | $2.3 \times 10^{-7}$ |
| 13. N-(1-deoxytagatos-1-yl)-Val-Asp | $3.2 \times 10^{-7}$ |
| 14. N-(1-deoxyfructos-1-yl)-D-Ile | $3.4 \times 10^{-7}$ |

The enkastins can be administered singly or in combination, parenterally (i.v., s.c., i.m.) or orally in a physiologically tolerated medium. The dose which is to be administered is, as a rule, 0.1 to 10 mg/kg.

EXAMPLE 1

Obtaining the enkastins by fermentation (2,000 L)

To obtain the enkephalinase inhibitors according to the invention by fermentation, the producing microorganism Streptomyces albus ATCC 21838 was cultured-as customary in microbiology-from freeze-dried spores of this strain. Culture was initially carried out on a solid nutrient medium in sterile Petri dishes. Single colonies were subsequently further cultivated in slant tubes and, from these, cultures were carried out in Roux bottles for the mass production of spores required for the fermentation.

Agar medium for passages on solid nutrient media:

| | |
|---|---|
| Dextrin | 15.0 g/l |
| Sucrose | 2.0 g/l |
| Meat extract | 1.0 g/l |
| Yeast extract | 2.0 g/l |
| Sodium chloride | 0.5 g/l |
| $K_2HPO_4$ | 0.5 g/l |
| $FeSO_4.7H_2O$ | 0.01 g/l |
| Agar | 2.0 g/l |
| pH | 7.3 |
| Sterilisation at 120° C., 20 minutes | |
| Incubation at 30° C., 9 days. | |

The spores rinsed out of one Roux bottle were taken up in 100 ml of sterile water and used as inoculum for the preparation of the first, submerged, vegetative preliminary vegetation stage (working volume 1.2 L).

Preliminary stage medium:

| | |
|---|---|
| Soluble starch | 4.0 g/l |
| Glucose | 1.0 g/l |
| Casein-peptone | 1.0 g/l |
| Cornsteep liquor | 0.4 g/l |
| Soybean flour | 0.4 g/l |
| $(NH_4)_2SO_4$ | 0.8 g/l |
| pH | 8.3 |
| Sterilisation at 120° C., 20 minutes | |
| Incubation at 18° C., 2 days | |
| Shaker at 150 rpm and amplitude of 5 cm. | |

After 48 hours, the contents of one Fernbach bottle containing the first preliminary culture obtained in this way (see above) was used as inoculum for the second preliminary culture, amounting to 200 L, with the preliminary culture medium (see above) being used once again. The sterilisation time was 30 minutes. Incubation lasted 48 hours at 28° C., while stirring at a circumferential velocity of 5 m/sec. and with an aeration rate of 0.1 vvm.

The contents of the second preliminary culture was used as inoculum for the 200 L of main fermentation medium.

Main fermentation medium:

| | |
|---|---|
| Peanut flour | 30.0 g/l |
| Cornsteep, solid | 10.0 g/l |
| Corn starch | 20.0 g/l |
| Dextrin | 40.0 g/l |
| $(NH_4)_2SO_4$ | 5.0 g/l |
| $MgSO_4.7H_2O$ | 5.0 g/l |
| $CaCO_3$ | 8.0 g/l |
| pH | 6.8 |
| Sterilisation at 120° C., 50 minutes | |

Sterilisation at 120° C., 50 minutes

The main fermentation was carried out at 28° C., stirring at a circumferential velocity of 4 m/sec and with an aeration rate of 0.6 vvm. Production of the inhibitors according to the invention started after 4 days and reached its maximum after 10 to 12 days. The fermenter was harvested after the fermentation maximum had been reached. The yield of enkastin complex of the formula I was between 5 and 10 µg/l of culture solution.

EXAMPLE 2

Isolation of the enkastins from the culture solution

A filter press was used to remove the mass of cells from 2,000 l of fermentation solution from Example 1, and the clear liquid was extracted twice with 600 l of n-butanol each time. The defatted aqueous phase was subsequently concentrated to 150 l in vacuo in a falling film evaporator, and then this concentrate was diluted with 600 l of methanol. This resulted in a pale, flocculent precipitate which was sedimented by centrifugation and discarded. The aqueous methanolic supernatant was again concentrated in vacuo and dried to produce 18 kg of a brown sticky mass. Subsequently, adsorption on 70 l of ®Dowex 50 WX 2 (acid form) cation exchanger was carried out in aqueous medium, the loaded exchanger was washed with pure water, and the inhibitors were desorbed with 0.5M ammonium hydroxide solution. The enkephalinase-inhibiting eluates were collected and freeze-dried (3.5 kg). The amphoteric compounds were separated out of this by an analogous procedure on 70 l of ®Amberlite IRA-68 anion exchanger. In this case, the enkastins were eluted with 0.5M acetic acid. Freeze-drying of the eluates with inhibitory activity yielded 320 g of dry product. Gel chromatography on ®Sephadex G-15 and freeze-drying of the active material yielded 30 g of crude enkastin complex.

EXAMPLE 3

Fractionation of the enkastin components 150 mg of the material obtained as in Example 2 were dissolved in 1 ml of water, and the solution was applied to a steel column (with the internal dimensions 3.2×25 cm$^2$) packed with RP-18 reversed phase silica gel. Elution was initially with 0.05% strength trifluoroacetic acid (TFA), followed, after a running time of 40 minutes, by a linear gradient of acetonitrile in 0.05% strength TFA. The eluate from the column was monitored by determination of the ultraviolet absorption at 200 nm. A large number of sharply separated substances was eluted from the column during the elution, and each of these was collected separately. They were freeze-dried and examined. Peaks 2, 3, 4, 5, 7, 8, 11, 13, 16, 18 and 21 proved to have enkephalinase-inhibitory activity.

Peak 3 (retention time 5 minutes 8 seconds) contained enkastin AD. Amino acid analysis revealed equimolar amounts of alanine and aspartic acid. The molecular weight determined from the FAB mass spectrum was 366, corresponding to the molecular formula $C_{13}H_{22}N_2O_{10}$. The structure indicated above was determined by $^2D$ NMR experiments.

Figure 1:
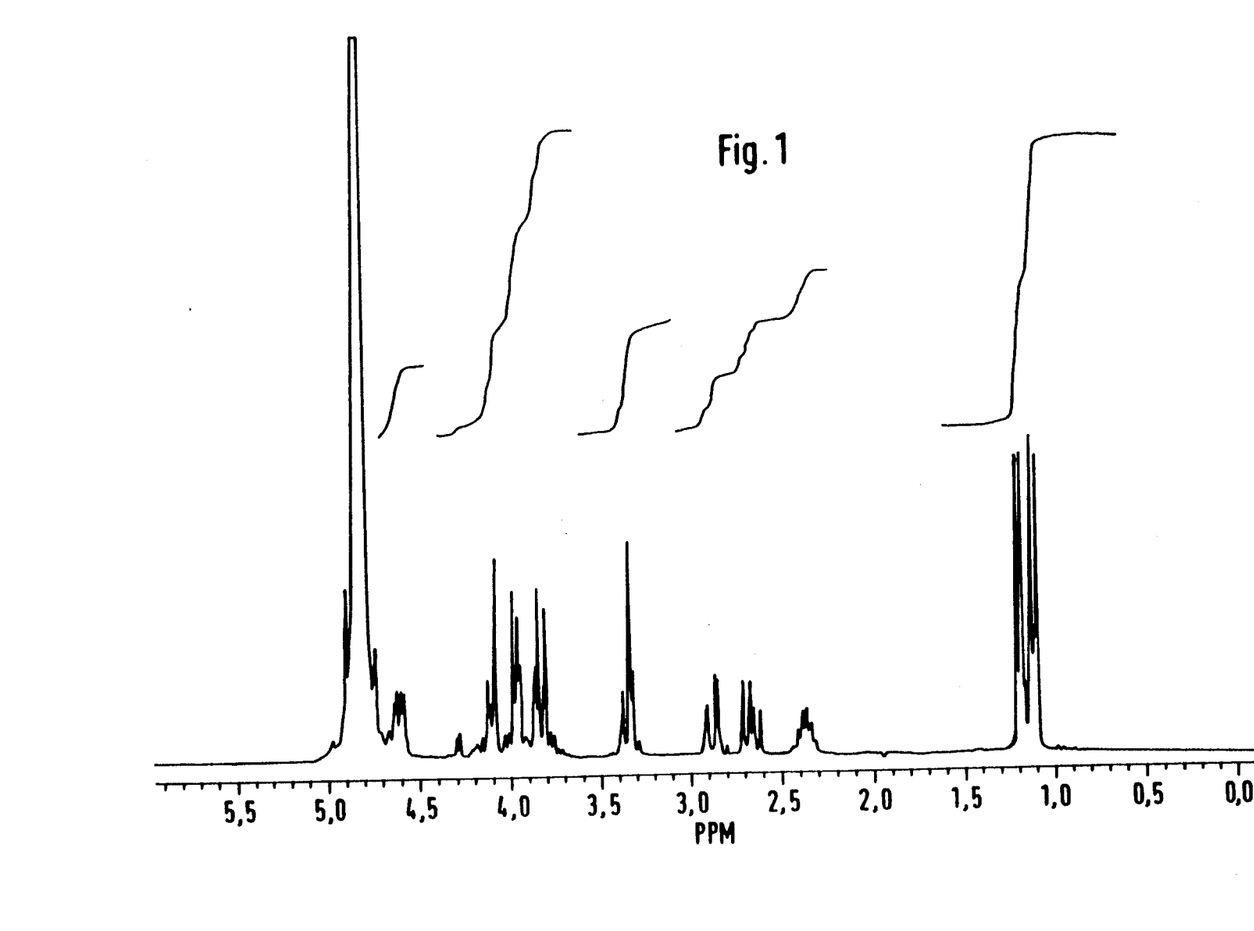
FIG. 1: $^1$H NMR spectrum of enkastin VD (Fru-Val-Asp) from Example 3.

Peak 4 (retention time 5 minutes 21 seconds) yielded small amounts of enkastin VD with the molecular weight 394, corresponding to the molecular formula $C_{15}H_{26}N_2O_{10}$. FIG. 1 shows the 270 MHz $^1H$ NMR spectrum of enkastin VD.

Peak 7 (retention time 7 minutes 20 seconds) contained enkastin AE, molecular weight 380, molecular formula $C_{14}H_{24}N_2O_{10}$.

Peak 11 (retention time 8 minutes 10 seconds) yielded enkastin VE, molecular weight 408, $C_{16}H_{28}N_2O_{10}$, having the amino acids Val and Glu, and peak 13 (retention time 18 minutes 40 seconds) yielded enkastin ID, molecular weight 408, $C_{15}H_{28}N_2O_{10}$, having Ile and Asp as amino acids. Peak 16 (retention time 22 minutes) contained enkastin IE, molecular weight 422, $C_{17}H_{30}N_2O_{10}$.

EXAMPLE 4

Synthesis of N-(1-deoxyfructopyranos-1-yl)-isoleucyl-aspartic acid 30 g of anhydrous D-glucose were dissolved together with 3 g of isoleucyl-aspartic acid in 1.2 l of methanol, and 200 mg of NaHCO$_3$ were added. The mixture was subsequently heated under reflux for 2 hours. The water which had formed was then removed by distillation with butanol, and the reaction mixture was diluted with methanol and again heated for 2 hours. After completion of the reaction, solvent was removed from the solution in vacuo, and the residue, in 300 ml of water, was applied to a 600 ml-capacity chromatography column (diameter 5 cm) packed with QAE- ®Sephadex A-25. Whereas the excess glucose was located in the fore-run, it was possible to obtain selectively N-(1-deoxyfructopyranos-1-yl)-isoleucylaspartic acid using an acetic acid gradient (0 to 0.5 molar). These eluates from the column were collected and freeze-dried.

Yield: 720 mg of a white amorphous powder.

$^1$H NMR spectrum [ppm]: 4.43; 2.69; 2.48; 3.84; 1.93; 1.50; 1.26; 0.93 and 0.89 and, caused by the peptide part of the molecule; 3.93; 3.91; 3.79; 3.66; 3.65; 3.17; and 3.14 from the glycan part of the inhibitor, corresponding to the signals of the natural enkastin ID compound.

$^{13}$C NMR spectrum [ppm]: 54.63; 40.49; 66.79; 37.13; 26.12; 14.61 and 11.75 (peptide part) and at 96.55; 70.91; 70.40; 69.96; 64.87 and 53.43 (glycan part).

The infrared absorption spectrum shows bands at 3400, 2920, 2860, 1595, 1400 and 1080 cm$^{-1}$.

EXAMPLE 5

Synthesis of N-(1-deoxyfructopyranps-1-yl)-phenylalanyl-aspartic acid 200 mg of phenylalanyl-aspartic acid were suspended with 1.5 g of D-glucose in 100 ml of methanol, 20 mg of NaHCO$_3$ were added, and the mixture was boiled for 2 hours. The reaction mixture was then further processed and purified on the QAE ®Sephadex A-25 column (1.8 cm×23 cm, 60 ml) as described in Example 4, and then salts were removed. 26 mg of N-(1-deoxyfructopyranos-1-yl)-phenyl-alanyl-aspartic acid were obtained.

270 MHz $^1$H NMR spectrum (D$_2$O) of enkastin FD: 3.03; 2.96; 3.65; 3.81; 3.94; 3.99; 3.67; 3.84; 3.17; 3.08; 7.36; 4.43; 2.71; 2.51 ppm.

EXAMPLE 6

Synthesis of N-(1-deoxyfructopyranos-1-yl)-isoleucyl-serine 200 mg of isoleucyl-serine were reacted with 1.5 g of D-glucose, and the reaction product was purified, as described in Example 5. 12 mg of N-(1-deoxyfructopyranos-1-yl)-Ile-Ser-OH were produced. The structure was confirmed by chemical and spectroscopic investigations.

270 MHz $^1$H NMR spectrum (D$_2$O) of enkastin IS: 3.38; 3.34; 3.85; 3.98; 4.15; 4.09; 3.82; 4.45; 4.00; 3.95; 3.97; 2.15; 1.08; 1.79; 1.43; 1.06 ppm.

EXAMPLE 7

Synthesis of N-(1-deoxyfructopyranos-1-yl)-isoleucyl-asparagine 300 mg of isoleucyl-asparagine were reacted with 1.5 g of D-glucose, and the reaction product was purified, as described in Example 5. 90 mg of N-(1-deoxyfructopyranos-1-yl)-Ile-Asn were produced.

The 270 MHz $^1$H NMR spectrum (D$_2$O) shows the following characteristic signals of Enkastin IN: 3.05; 4.07; 3.95; 3.79; 4.08 and 3.78 ppm as well as 3.60; 1.89; 1.53; 1.28; 0.97 and 0.93 ppm furthermore 4.54; 2.84 and 2.69 ppm.

EXAMPLE 8

Synthesis of N-(1-deoxytagatopyranos-1-yl)-valyl-aspartic acid

Reaction of 150 mg of valyl-aspartic acid with 1 g of galactose, and purification, were carried out as in Example 5. 22 mg of N-(1-deoxytagatopyranos-1-yl)-valyl-aspartic acid resulted.

The 270 MHz $^1$H NMR spectrum measured in D$_2$O exhibits the following signals: 3.16; 3.17; 4.02; 3.91; 2.68; 3.66 and 3.86 ppm as well as 2.63; 2.22; 1.09 and 1.05 ppm furthermore 4.56; 2.81 and 2.60 ppm.

EXAMPLE 9

Synthesis of N-(1-deoxyfructopyranos-1-yl)-D-valine 10 g of anhydrous D-valine and 75 g of anhydrous D-glucose were dissolved in a mixture of 500 ml of dry methanol, 100 ml of dimethyl sulfoxide and 150 ml of pyridine, and the solution was boiled under reflux for 2.5 hours. After this time, the honey-colored reaction solution was concentrated in vacuo in a rotary evaporator in order to remove the methanol and the water formed during the reaction. The concentrate, which still contained pyridine, was left to stand overnight at room temperature, excluding moisture, in order to complete the reaction.

The product was purified by dissolving the reaction mixture in water, adjusting the pH to 9 with sodium hydroxide solution, and applying the solution to a prepared ®QAE-Sepharose FF column (5 cm×50 cm) equilibrated at ph 9. The ion exchanger was then first washed with 0.1% ammonium acetate solution, pH 9.0, and subsequently a 0.2 molar acetic acid gradient was applied. The eluate from the column was collected in fractions, and the fractions were examined individually. The fractions with a pH of 5.3 to 5.5 contained the newly synthesized inhibitor in pure form. They were combined and dried. Salts were removed using ®Sephadex G-15 molecular sieve to result in the salt-free product. Crystallization from water-methanol yielded 7 g of N-(1-deoxyfructopyranos-1-yl)-D-valine. Melting point 125°–126° C.

EXAMPLE 10

Synthesis of N-(1-deoxyfructopyranos-1-yl)-D-isoleucine

A dry mixture of 40 ml of methanol and 10 ml of pyridine was added to 100 mg of dry D-isoleucine together with 300 mg of anhydrous glucose, and reaction and purification were carried out as described in Example 9, but making use of smaller-volume chromatography columns. Crystallization of the final product yielded 110 mg of N-(1-deoxyfructopyranos-1-yl)-D-isoleucine. Melting point 142°–144° C.

EXAMPLE 11

Synthesis of N-(1-deoxyfructopyranos-1-yl)-D-valyl-aspartic acid 300 ml of pyridine and 3 l of methanol were added to 10 g of D-valyl-aspartic acid and 50 g of anhydrous D-glucose, and the stirred mixture was boiled for 2.5 hours. The reactants gradually dissolved during this time, and the reaction mixture assumed a yellow-gold color. After the reaction was complete, the mixture was concentrated in vacuo and further processed as described in Example 9. Freeze-drying resulted in 13.5 g of amorphous N-(1-deoxyfructopyranos-2-yl)-D-valyl-aspartic acid.

Figure 2:
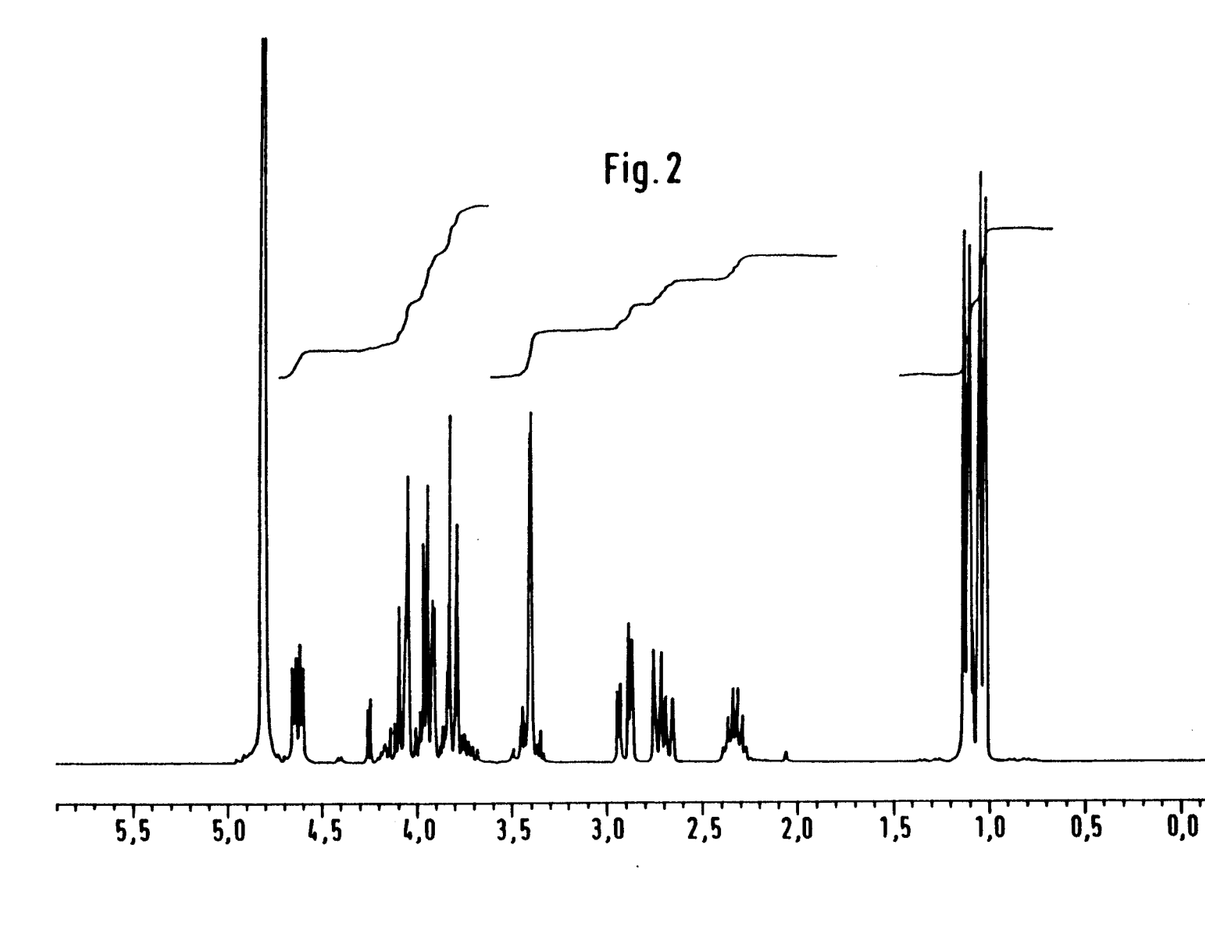
FIG. 2: $^1$H NMR spectrum of enkastin (D)VD (Fru-D-Val-Asp) from Example 11.

FIG. 2 shows the 270 MHz $^1$H NMR spectrum ($D_2O$) of enkastin D(VD).

EXAMPLE 12

Synthesis of N-(1-deoxyfructopyranos-1-yl)-D-isoleucyl-aspartic acid

Reaction of 1 g of D-isoleucyl-aspartic acid with 5 g of D-glucose in 100 ml of methanol and 10 ml of pyridine, and purification, were carried out as described in Example 10. Freeze-drying resulted in 790 mg of a pure amorphous material.

Figure 3:
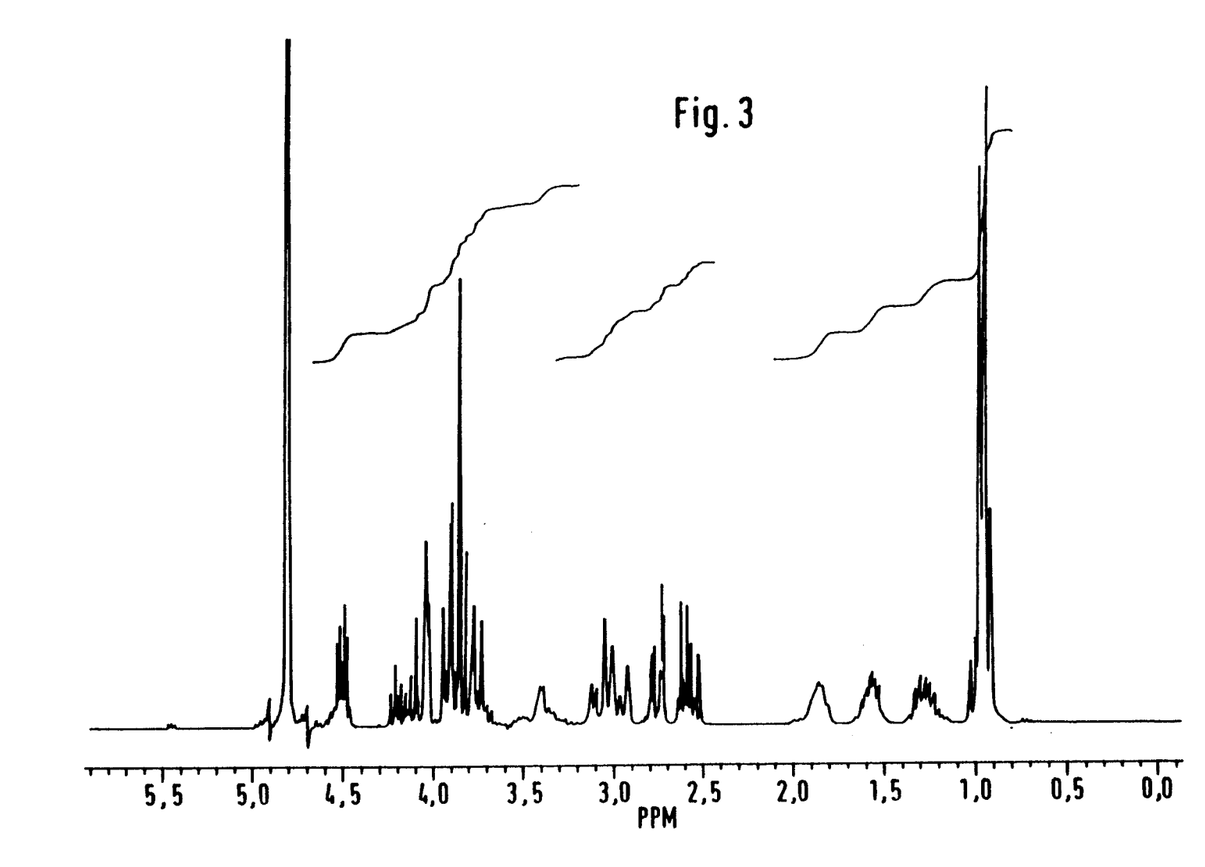
FIG. 3: $^1$H NMR spectrum of enkastin (D)ID (Fru-D-Ile-Asp) from Example 12.

The 270 MHz $^1$H NMR spectrum ($D_2O$) of enkastin (D)ID is depicted in FIG. 3.

EXAMPLE 13

Synthesis of mono-tert.-butyl N-(1-deoxyfructopyranos-1-yl)-isoleucyl-aspartate Reaction of 7 g of mono-tert.-butyl isoleucyl-aspartate, and purification, were carried out as described in Example 11. The resulting freeze-dried product was 5.8 g of amorphous mono-tert.-butyl N-(1-deoxyfructopyranos-1-yl)-isoleucyl-aspartate.

Figure 4:
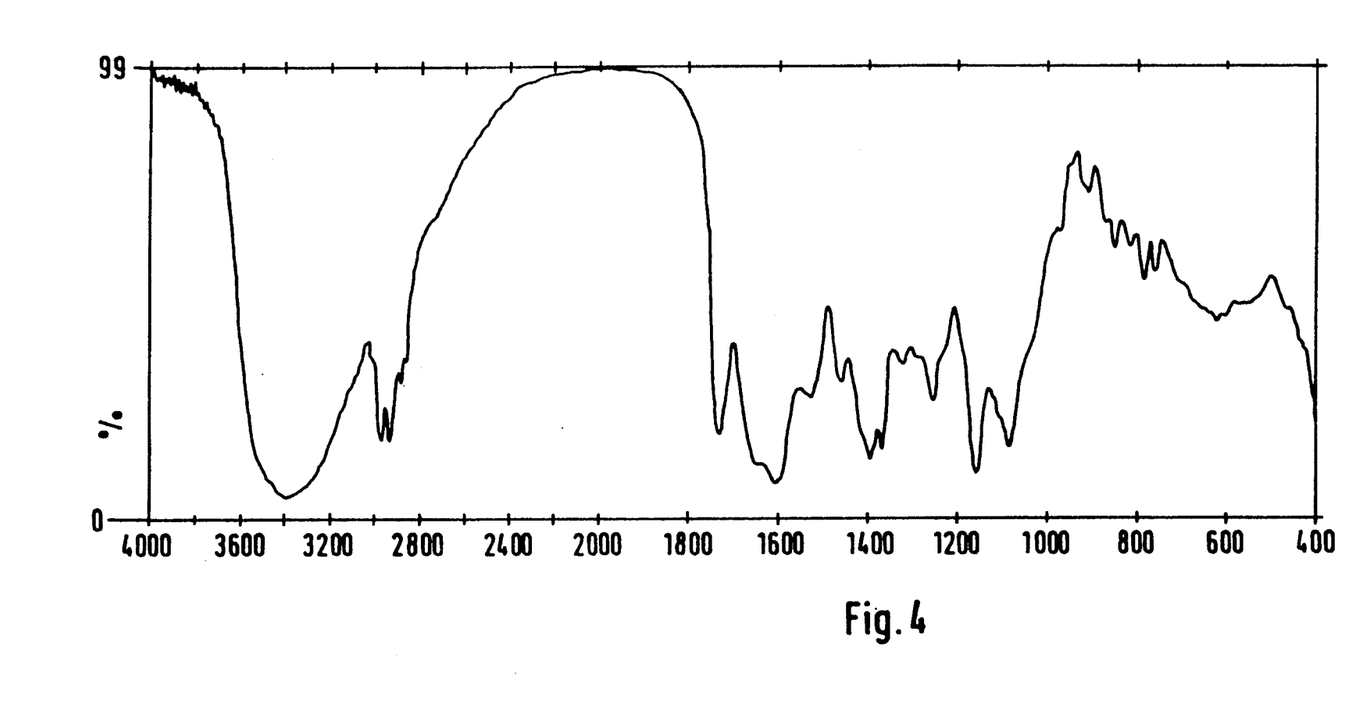
FIG. 4: IR spectrum of enkastin ID-OtBu (Fru-Ile-Asp-OtBu) from Example 13.

The IR spectrum of enkastin ID-OtBu is depicted in FIG. 4.

EXAMPLE 14

Synthesis of N-(1-deoxyfructopyranos-1-yl)-D-hexahydrophenylglycyl-aspartic acid 300 mg of D-hexahydrophenylglycyl-aspartic acid (D-Hhp-Asp) were reacted with 1.5 g of glucose as described in Example 10. 260 mg of amorphour N-(1-deoxyfructopyranos-1-yl)-D-Hhp-Asp were obtained.

Figure 5:
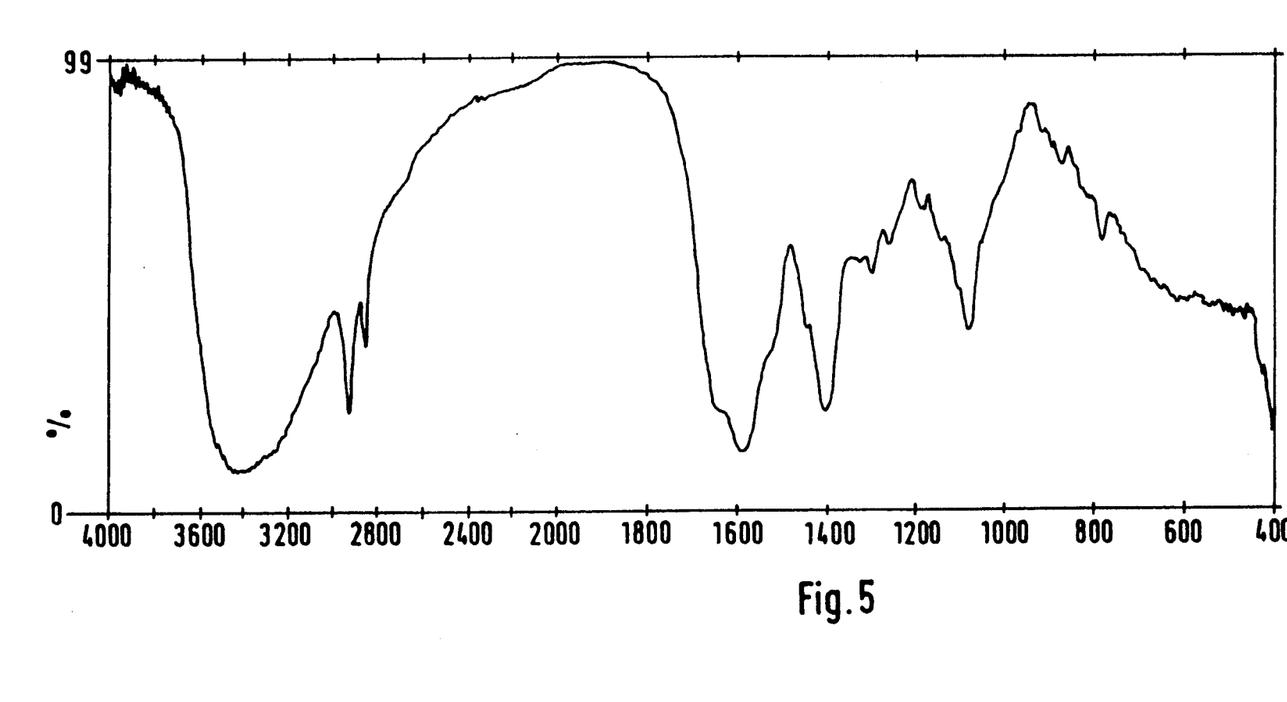
FIG. 5: IR spectrum of (Fru-D-Hhp-Asp) from Example 14.

The IR spectrum is shown in FIG. 5.

The $^1$H NMR spectra were recorded at 270 MHz in $D_2O$. The IR spectra are FTIR (Fourier Transform Infrared) absorption spectra recorded in KBr disks.

We claim:

1. A compound of the formula I $$\text{Sacch—A—B—R} \qquad (I)$$

in which

Sacch denotes fructosyl or 1-deoxyfructopyranos-1-yl;

A denotes Ile, Phe, Leu, Val, Gly, Cys, Ala or Hhp, wherein each residue is in the L or D form or—where B is absent—each of the preceding residues is in the D form;

B is absent or denotes Asp, Asx, Glu or Ser, wherein each residue is in the L- or D-form; and R denotes hydroxyl;

with the exception of N-(1-deoxy-β-D-fructopyranos-1-yl)Gly-Ser-OH and the physiologically tolerated salts thereof.

2. A compound of the formula I as claimed in claim 1, in which

Sacch denotes fructosyl or 1-deoxyfructopyranos-1-yl;

A denotes Ile, Leu, Val, Cys or Hhp, wherein each residue is in the D form;

B denotes Asp, Asx, Glu or Ser, wherein each residue is in the L- or D-form; and R denotes hydroxyl;

and the physiologically tolerated salts thereof.

3. A method of treating painful conditions by administering an effective amount of a compound of the formula I as claimed in claim 1 or a pharmaceutically acceptable salt thereof.

4. N-(1-deoxyfructopyranos-1-yl)-D-Val-Asp and its physiologically tolerated salts.

5. N-(1-deoxyfructopyranos-1-yl)-D-Ile-Asp and its physiologically tolerated salts.

* * * * *